US006989371B1

(12) United States Patent
Burman et al.

(10) Patent No.: US 6,989,371 B1
(45) Date of Patent: Jan. 24, 2006

(54) BOMBESIN ANALOGS FOR TREATMENT OF CANCER

(75) Inventors: Anand C. Burman, Ghaziabad (IN); Sudhanand Prasad, Ghaziabad (IN); Rama Mukherjee, Ghaziabad (IN); Manu Jaggi, Ghaziabad (IN); Anu T. Singh, Ghaziabad (IN); Archna Mathur, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 21 days.

(21) Appl. No.: 09/630,333

(22) Filed: Jul. 31, 2000

Related U.S. Application Data

(63) Continuation-in-part of application No. 09/248,381, filed on Feb. 11, 1999, now Pat. No. 6,492,330, and a continuation-in-part of application No. 09/248,382, filed on Feb. 10, 1999, now abandoned, and a continuation-in-part of application No. 08/727,679, filed on Oct. 8, 1996, now Pat. No. 6,156,725.

(60) Provisional application No. 60/080,433, filed on Apr. 2, 1998.

(30) Foreign Application Priority Data

| Aug. 16, 1996 | (IN) | ............................. 1822/DEL/96 |
| Feb. 11, 1998 | (IN) | ............................. 342/DEL/98 |
| Feb. 11, 1998 | (IN) | ............................. 343/DEL/98 |
| Feb. 24, 2000 | (IN) | ............................. 147/DEL/2000 |

(51) Int. Cl.
*A61K 38/00* (2006.01)
*C07K 7/00* (2006.01)

(52) U.S. Cl. .............................. 514/16; 514/2; 514/14; 514/15; 530/327; 530/328; 435/7.1

(58) Field of Classification Search .................... 514/2, 514/15, 16, 14; 530/328, 327, 329; 435/7.1
See application file for complete search history.

(56) References Cited

U.S. PATENT DOCUMENTS

| 5,084,555 A | 1/1992 | Coy et al. .................... 530/328 |
| 5,217,955 A | 6/1993 | Bogden et al. ................ 514/12 |
| 5,369,094 A | 11/1994 | Schally et al. ................ 514/15 |
| 5,428,019 A | 6/1995 | Edwards et al. ............... 514/16 |
| 5,565,431 A | 10/1996 | Lipps et al. ................... 514/21 |
| 5,601,992 A | 2/1997 | Lerner et al. ................. 435/7.2 |
| 5,620,955 A | 4/1997 | Knight et al. ................. 514/14 |

(Continued)

FOREIGN PATENT DOCUMENTS

| EP | 0315367 | 5/1989 |
| EP | 0345990 | 12/1989 |
| EP | 0468497 | 1/1992 |
| EP | 0835662 | 4/1998 |
| WO | 0047221 | 8/2000 |

OTHER PUBLICATIONS

Jaine, Sci. Amer., vol. 271, pp. 58-65, Jul 1994.*
Curti, Critical Reviews in Oncology/Hematology, vol. 14, pp. 14-29, 1993.*
Ross et al., Immunology Today, vol. 11, No. 6, 1990.*
Simen, in Rodent Tumor Models in Experimental Cancer Therapy, edited by Robert F. Kallman, published by Pregamon Press, 1987, pp. 12-15.*
Trott, in Rodent Tumor Models in Experimental Cancer Therapy, edited by Robert F. Kallma, published by Pregamon Press, 1987, pp. 6-11.*
G. Halmos et al.; Characterization of Bombesin/Gastrin-Relating Peptide Receptors in Membranes of MKN45 Human Gastric Cancer; Cancer Letters 85 (1994) 111-118.
H. Reile et al.; Characterization of High-Affinity Receptors for Bombesin/Gastrin Releasing . . . Cells; The Prostate 25:29-38 (1994).
I. Zachary, et al.; Bombesin, Vasopressin, and Endothelin Rapidly Stimulate Tyrosine Phosphorylation in Intact Swiss 3T3 Cells; PNAS; vol. 88 pp. 4577-4581, Jun. 1991.
K. Szepeshazi et al.; Combination Treatment of Nitrosamine-Induced . . . Antagonist; Int'l. Journal of Pancreatology; vol. 16, Nos. 2-3, 141-149, Oct.-Dec. 1994.
K. Heiling et al.; Transforming Growth Factor . . . Colonic Epithelium; May 1986.
Frucht, et al.; Cancer Research 52 : 1114-1122, Mar. 1, 1992.
Willard R. Chappell, et al. "Extrapolation of Toxicological and Pharmacological Data From Animals to Humans" Advances in Drug Research, vol. 20 pp. 1-117.
Yuichi Sugiyama, et al. "Receptor-Mediated Disposition of Polypeptides: . . . " Journal of Controlled Release, vol. 13 (1990) pp. 157-174 Elsevier Science Publishers B.V., Amsterdam.
Joyce Mordenti "Dosage Regimen Design For Pharmaceutical Studies Conducted in Animals" Journal of Pharmaceutical Sciences vol. 75, No. 9, Sep. 1986.

(Continued)

*Primary Examiner*—Jon Weber
*Assistant Examiner*—Chih-Min Kam
(74) *Attorney, Agent, or Firm*—Ladas & Parry

(57) ABSTRACT

The present invention encompasses novel peptides that are antagonists to bombesin and bombesin like peptides and are useful in the treatment of cancer. The invention particularly relates to the design and synthesis of the novel peptides incorporating α,α-amino acids in a site specific manner. The invention encompasses methods for the generation of these peptides, compositions containing the peptides and the pharmacological applications of these peptides especially in the treatment and prevention of cancer.

22 Claims, No Drawings

U.S. PATENT DOCUMENTS

| | | | |
|---|---|---|---|
| 5,620,959 | A | 4/1997 | Leban et al. .................. 514/16 |
| 5,723,578 | A | 3/1998 | Coy et al. .................... 530/326 |
| 5,834,433 | A | 11/1998 | Krstenansky ................ 514/16 |
| 6,492,330 | B1 * | 12/2002 | Mukherjee et al. ........... 514/12 |
| 2003/0050233 | A1 * | 3/2003 | Burman et al. ............... 514/12 |

OTHER PUBLICATIONS

Harold Boxenbaum, et al. "First-Time-In-Human Dose Selection: Allometric Thoughts and Perspectives" Pharmacokinetics Series J. Clin Pharmacol 1995; vol. 35: pp. 957-966.

* cited by examiner

SEQUENCE LISTING

<160> NUMBER OF SEQ ID NOS: 12

<210> SEQ ID NO 1
<211> LENGTH: 14
<212> TYPE: PRT
<213> ORGANISM: Bombina bombina

<400> SEQUENCE: 1

Glu Gln Arg Leu Gly Asn Gln Trp Ala Val Gly His Leu Met
 1               5                  10

<210> SEQ ID NO 2
<211> LENGTH: 10
<212> TYPE: PRT
<213> ORGANISM: Sus barbatus

<400> SEQUENCE: 2

Gly Asn His Trp Ala Val Gly His Leu Met
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (6)
<223> OTHER INFORMATION: /product = alpha-aminoisobutyric acid/label =
      Aib

<400> SEQUENCE: 3

Xaa Gln Trp Ala Val Xaa His Leu
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = alpha-aminoisobutyric acid/label =
      Aib

<400> SEQUENCE: 4

Xaa Gln Trp Xaa Val Gly His Leu
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = D-phenylalanine/label = D-Phe

```
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (6)
<223> OTHER INFORMATION: /product = alpha-aminoisobutyric acid/label =
      Aib

<400> SEQUENCE: 5

Xaa Gln Xaa Ala Val Xaa His Leu
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = alpha-aminoisobutyric acid/label =
      Aib

<400> SEQUENCE: 6

Xaa Gln Trp Xaa Val Gly His Ile
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (6)
<223> OTHER INFORMATION: /product = alpha-aminoisobutyric acid/label =
      Aib

<400> SEQUENCE: 7

Xaa Gln Trp Ala Val Xaa His Ile
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (3)
<223> OTHER INFORMATION: /product = D-tryptophan/label = D-Trp
<221> NAME/KEY: MOD_RES
<222> LOCATION: (6)
<223> OTHER INFORMATION: /product = alpha,alpha-di-n-
      propylglycine/label = Dpg

<400> SEQUENCE: 8

Xaa Gln Xaa Ala Val Xaa His Leu
 1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (4)
<223> OTHER INFORMATION: /product = alpha,alpha-di-ethyl glycine = Deg

<400> SEQUENCE: 9

Xaa Gln Trp Xaa Val Gly His Leu
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = D-phenylalanine/label = D-Phe
<221> NAME/KEY: MOD_RES
<222> LOCATION: (6)
<223> OTHER INFORMATION: /product = 1-Aminocyclopentane carboxylic
      acid/label = Ac5c

<400> SEQUENCE: 10

Xaa Gln Trp Ala Val Xaa His Leu
 1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<221> NAME/KEY: MOD_RES
<222> LOCATION: (1)
<223> OTHER INFORMATION: /product = Butanoyl-D-phenylalanine/label =
      Butanoyl-D-Phe
<221> NAME/KEY: MOD_RES
<222> LOCATION: (6)
<223> OTHER INFORMATION: /product = alpha-aminoisobutyric acid/label =
      Aib

<400> SEQUENCE: 11

Xaa Gln Trp Ala Val Xaa His Leu
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated
<221> NAME/KEY: MOD_RES
<222> LOCATION: (1)
<223> OTHER INFORMATION: /product = Octanoyl-D-phenylalanine/label =
      Octanoyl-D-Phe
<221> NAME/KEY: MOD_RES
<222> LOCATION: (6)
<223> OTHER INFORMATION: /product = alpha-aminoisobutyric acid/label =
      Aib
```

```
<400> SEQUENCE: 12

Xaa Gln Trp Ala Val Xaa His Leu
 1               5
```

BOMBESIN ANALOGS FOR TREATMENT OF CANCER

This application is a continuation-in-part of U.S. application Ser. No. 09/248,382, filed on Feb. 10, 1999, now abandoned; This application is a continuation-in-part of U.S. application Ser. No. 09/248,381, filed on Feb. 11, 1999, now U.S. Pat. No. 6,492,330, which claims benefit of U.S. Provisional Application Ser. No. 60/080,433, filed on Apr. 2, 1998; This application is a continuation-in-part of U.S. application Ser. No. 08/727,679, filed on Oct. 8, 1996, now U.S. Pat. No. 6,156,725.

FIELD OF INVENTION

The present invention encompasses novel peptides that are antagonists to bombesin and bombesin like peptides and are useful in the treatment of cancer. The invention particularly relates to the design and synthesis of the novel peptides incorporating α,α-amino acids in a site specific manner. The invention encompasses methods for the generation of these peptides, compositions containing the peptides and the pharmacological applications of these peptides especially in the treatment and prevention of cancer.

BACKGROUND OF THE INVENTION

Bombesin is a 14 amino acid peptide which was first isolated from the skin of the frog Bombina bombina (Anastasi et al., Experientia, 1971, 27, 166) and has the sequence:

pGlu-Gln-Arg-Leu-Gly-Asn-Gln-Trp-Ala-Val-Gly-His-Leu-Met-$NH_2$ (SEQ ID NO: 1)

Gastrin releasing peptide (GRP) is a 27 amino acid peptide isolated from the porcine gut. The last ten amino acids at the C-terminus of gastrin releasing peptide correspond with one amino acid alteration (3) to the last ten amino acids of bombesin, viz:

H-Gly-Asn-His-Trp-Ala-Val-Gly-His-Leu-Met-$NH_2$ (SEQ ID NO:2).

It has been reported (J. H. Walsh and J. R. Reeve, Peptides 6, (3), 63–68, (1985)) that bombesin and bombesin-like peptides such as gastrin releasing peptide (GRP) are secreted by human small-cell lung cancer (SCI C) cells. It has been postulated (P. J. Woll and E. Rozengurt, PNAS 85, 1859–1863, (1988)) that gastrin releasing factor antagonists would bind competitively to bombesin receptors in animals and would therefore be of use in the treatment of SCLC and/or in the control of clinical symptoms associated with this disease and due to hypersecretion of this peptide hormone. Analogues of bombesin/GRP have been shown to inhibit the binding of gastrin releasing peptide to a SCLC cell line and to inhibit the growth of SCLC cells in-vitro and in-vivo (S. Mahmoud et al., Cancel Research, 1991, 51, 1798; Moody T W et al., Life Sci. 1995, 56, 521; Moody T W et al., Peptides, 1996, 17, 1337). After Bombesin/GRP cell receptors were established on SCLC cells, receptors were also found to be present on human prostate cells. Relic H et al., (Prostate, 1994, 25: 29–38) showed that the PC-3 and DU-145 human prostate cancer cell lines possess specific high-affinity receptors for bombesin/GRP and are suitable models for the evaluation of anti-neoplastic activity of new bombesin/GRP antagonists in the treatment of androgen-dependent prostate cancer. Bombesin also increased the penetration of the two human prostatic carcinoma cell lines, the relatively indolent LNCaP cells and the aggressively growing and invasive PC-3 cells, in an in vitro invasion of reconstituted basement membrane (Matrigel) (Hoosein N M et al., J Urol, 149(5): 1209–1213). High-affinity binding sites for GRP were found on human colorectal cancer tissue (Preston, SR. et al, Br. J. Can., 1995, 71, 1087), suggesting that bombesin-like peptides may have a role in the pathogenesis of colorectal cancer, and bombesin receptor antagonists may be of value in the treatment of receptor-positive tumours. Inhibitory effects of bombesin/GRP antagonist RC-3095 and somatostatin analogue RC-160 were also seen on growth of HT-29 human colon cancer xenografts in nude mice (Radulovic S et al., Acta Oncol, 1994, 33(6): 693–701).

Studies with the anti-bombesin/GRP antibodies lead to the hypothesis that it may be possible to disrupt the autocrine growth cycle of bombesin/GRP using designed peptide receptor antagonists. Since then several types of Bombesin antagonists have been reported. These antagonists have been defined by type and position of the substitutions of the natural sequence. Early receptor antagonists suffered from low potency, lack of specificity, and toxicity, which presented serious problems with their scientific and therapeutic use.

More recent work has concentrated on modification of the carboxy terminal (C-terminal) region of these peptides to interrupt the receptor interaction utilizing a variety of different types of C-terminal modified analogs. These have included incorporation of D-amino acids, non-peptide bonds for example (psi. $CH_2NH$), amide, and ester modifications. These alterations gave rise to certain peptides having, improved characteristics (Staley J et al., Peptides, 1991, 12(1): 145–9; Coy D H et al., J Natl Cancer Inst Monogr. 13:992, 13: 133–9). Other patents that describes bombesin and related analogs are:

U.S. Pat. No. 5,834,433 (1998)
U.S. Pat. No. 5,723,578 (1998)
U.S. Pat. No. 5,620,959 (1997)
U.S. Pat. No. 5,620,959 (1997)
U.S. Pat. No. 5,428,019 (1999)
U.S. Pat. No. 5,399,094 (1994)
U.S. Pat. No. 5,084,555 (1992)

A Bombesin/GRP antagonist (RC-3940-II) was found to inhibit the proliferation of SW-1990 human pancreatic adenocarcinoma cells in vivo and in vitro (Qin, Y. et al., 1995, Int. J. Cancer, 63, 257). Similar effect was seen with bombesin/GRP antagonist RC-3095 on the growth of CFPAC-1 human pancreatic cancer cells transplanted to nude mice or cultured in vitro (Qin Y et al., Can Res, 1994, 54(4): 1035–41).

As reported earlier, the autocrine growth cycle of bombesin/GRP in SCLC can be disrupted by bombesin/GRP antagonists such as [Psi 13,14] bombesin. Several bombesin analogues were solid phase synthesized and incubated with intact SCLC cells at 37° C. in RPMI medium in a time course fashion (0–1080 minutes) to determine enzymatic stability. The proteolytic stability of the compounds was determined by subsequent HPLC analysis. [Psi 13, 14] Bombesin was found to be very stable to metabolic enzymes (TI/2=646 min.) and inhibited SCLC xenograft formation in vivo in a dose-dependent manner (Davis T P et al., Peptides, 1992, 13(2): 401–7).

Female athymic nude mice bearing xenografts of the MCF-7 MIII human breast cancer cell line were treated for 7 weeks with bombesin/GRP antagonist (DTpi6, Leu3, psi[$CH_2NH$]—Leu14) bombesin (6–14)(RC-3095) injected administered biweekly in the form of microgranules releasing 45 μg/day. After 2 weeks of treatment, a significant inhibition of tumor volume was observed in the groups treated with RC-3095 alone or in combination with SB-75 (Yano T et al., Cancer, 1994, 73(4): 1229–38).

Pinski J. et al., (Int. J. Cancer, 1994, 57(4): 574–580), demonstrated for the first time that the growth of gastrin-responsive human gastric carcinoma MKN45 cell line xenografts in nude mice could be inhibited not only by somatostatin analogues, but also by administration of modern bombesin/GRP antagonists, such as RC-3095, or a combination of these. RC-3095 also effectively inhibited tumor growth in nude mice bearing xenografts of the human gastric cancer cell line Hs746T (Qin Y et al., J Cancer Res Clin Oncol, 1994,120(9):519–528).

This invention describes the preparation and use of peptide analogs of bombesin/GRP using constrained amino acids and their use for cancer therapy, alone, or in combination or as an adjunct to or with other chemotherapeutic agents and compounds.

The design of conformationally constrained bioactive peptide derivatives has been one of the widely used approaches for the development of peptide-based therapeutic agents. Non-standard amino acids with strong conformational preferences may be used to direct the course of polypeptide chain folding, by imposing local stereochemical constraints, in de novo approaches to peptide design. The conformational characteristics of α,α-dialkylated amino acids have been well studied. The incorporation of these amino acids restricts the rotation of φ, ψ angles, within the molecule, thereby stabilizing a desired peptide conformation. The prototypic member of α,α-dialkylated aminoacids, α-aminoisobutyric acid (Aib) or α,α-dimethylglycine has been shown to induce (β-turn or helical conformation when incorporated in a peptide sequence (Prasad and Balaram, (1984); CRC Crit. Rev. Biochem. 16, 307–347; Karle and Balaram (1990) Biochemistry 29, 6747–6756). The conformational properties of the higher homologs of α,α-dialkylated amino acids such as diethylglycine (Deg), di-n-propylglycine (Dpg) and di-n-butylglycine (Dbg) as well as the cyclic side chain analogs of α,α-dialkylated amino acids such as 1-aminocyclopentane carboxylic acid (Ac5c). 1-aminocyclohexane carboxylic acid (Ac6c), 1-aminocycloheptane carboxylic acid (Ac7c) and 1-aminocyclooctane carboxylic acid (Ac8c) have also been shown to induce folded conformation (Prasad et al., (1995), Biopolymers 35, 11–20; Karle et al., (1995); J. Amer. Chem. Soc. 117, 9632–9637). α,α-dialkylated amino acids have been used in the design of highly potent chemotactic peptide analogs (Prasad et al., (1996) Int. J. Peptidic Proteins RCS. 48, 312–318).

The present invention exploits the conformational properties of α,α -dialkylated amino acids for the design of biologically active peptide derivatives, taking bombesin as the model system under consideration. Furthermore, it has been shown that lipophilization of bioactive peptides improves their stability, bioavailability and the ability to permeate biomembranes (Dasgupta, P et al; 1999, Pharmaceutical Res. 16, 1047–1053; Gozes, 1, et al 1996, Proc. Natl. Acad. Sci. USA, 93, 427–432). In the present invention, we have also synthesized peptide derivatives having N-terminal alkanoyl groups from $C_2$–$C_{16}$ carbon atoms, which retain anticancer activity.

The present invention exploits the conformational properties of α,α-dialkylated amino acids for the design of biologically active peptide derivatives, taking bombesin as the model system under consideration. Furthermore, it has been shown that lipophilization of bioactive peptides improves their stability, bioavailability and the ability to permeate biomembranes (Dasgupta, P et al; 1999, Pharmaceutical Res. 16, 1047–1053; Goes, L, et al., 1996, Proc. Natl. Acad. Sci. USA, 93, 427–432).

Throughout the specification and claims the amino acid residues are designated by their standard abbreviations. Amino acids denote L-configuration unless otherwise indicated by D or DL appearing before the symbol and separated from it by a hypen. Throughout the specification and claims, the following abbreviations are used with the following meanings:

BOP: Benzotriazole-1-yl-oxy-tris-(dimethylamino)-phosphonium hexfluorophosphate
PyBOP: Benzotriazole-1-yl-oxy-tris-pyrrolidino-phosphonium hexofluorophospate
TBTU: 2-(1H-Benzotriazole-lyl)-1,1,3,3-tetramethyluronium tetrafluroborate
HBTU: O-Benzotriazole-N,N,N',N'-tetramethyl-uronium-hexofluoro-phosphate
HOBt: 1-Hydroxy Benzotriazole
DCC: Dicyclohexyl carbodiimide
DIPCDI: Diisopropyl carbodiimide
DHEA: Diisopropyl ethylamine
DMF: Dimethyl formamide
DCM: Dichloromethane
NMP: N-Methyl-2-pyrrolidinone
TFA: trifluoroacetic acid

SUMMARY OF INVENTION

The present invention provides novel polypeptides of the following general formula,

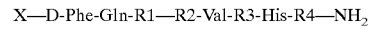
X—D-Phe-Gln-R1—R2-Val-R3-His-R4—$NH_2$ wherein X is acetyl or straight, branched, or cyclic alkanoyl group from 3–16 carbon atoms, or X is deleted,
R1 is Trp or D-Trp,
R2 is Ala, Aib or Deg,
R3 is Gly, Aib, Deg, Dpg or Ac5c,
R4 is Leu or Ile or a hydrolyzable carboxy protecting group; or a pharmaceutically acceptable salt of the polypeptide. At least one of R2 or R3 is a non-standard amino acid. The invention also encompasses methods for making the peptides, compositions containing the peptides and use of the peptides.

DETAILED DESCRIPTION OF THE INVENTION

The present invention provides novel polypeptides of the following general formula,
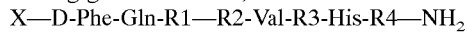
X—D-Phe-Gln-R1—R2-Val-R3-His-R4—$NH_2$ wherein X is acetyl or straight, branched, or cyclic alkanoyl group from 3–16 carbon atoms, or X is deleted,
R1 is Trp or D-Trp,
R2 is Ala, Aib or Deg,
R3 is Gly, Aib, Deg, Dpg or Ac5c.
R4 is Leu or Ile or a hydrolyzable carboxy protecting group; or a pharmaceutically acceptable salt of the polypeptide. At least one of R2 or R3 is a non-standard amino acid.

A hydrolyzable carboxy protecting group are those groups which on hydrolysis converts to carboxylic group such as —$COONH_2$, —(COOMe, etc.

The preferred alkanoyl groups are acetyl, n-butanoyl, n-hexanoyl, n-octanoyl, lauroyl, myristoyl, palmitoyl, iso-hexanoyl, cyclohexanoyl, cyclopentyl-carbonyl, n-heptanoyl, n-decanoyl, n-undecanoyl and 3,7-dimethyloctanoyl.

Salts encompassed within the term "pharmaceutically acceptable salts" refer to non-toxic salts of the compounds of this invention. Representative salts and esters include:

acetate, ascorbate, benzenesulfonate, benzoate, bicarbonate, bisulfate, bitartrate, borate, camsylate, carbonate, citrate, dihydrochloride, methanesulfonate, ethanesulfonate, p-toluenesulfonate, cyclohexylsulfamate, quinate, edetate, edisylate, estolate, esylate, fumaxate, gluconate, glutamate, glycerophophates, hydrobromide, 5 hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, trifluoroacetate, tosylate and valerate.

Other salts include Ca, Li, Mg, Na and K salts; salts of amino acids such lysine or arginine; guanidine, diethanolamine or choline; ammonium, substituted ammonium salts or aluminum salts.

The salts can be prepared by standard techniques.

Preferred peptides of this invention are:

D-Phe-Gln-Trp-Ala-Val-Aib-His-Leu-N$_2$ (SEQ ID NO:3)

D-Phe-Gln-Trp-Aib-Val-Gly-His-Leu-NH$_2$ (SEQ ID NO:4)

D-Phe-Gln-D-Trp-Ala-Val-Aib-His-Leu-NH$_2$ (SEQ ID NO:5)

D-Phe-Gln-Trp-Ala-Val-Gly-His-Ile-NH$_2$, (SEQ ID NO:6)

D-Phe-Gln-Trp-Ala-Val-Aib-His-Ile-NH$_2$ (SEQ ID NO:7)

D-Phe-Gln-D-Trp-Ala-Val-Dpg-His-Leu-NH$_2$ (SEQ ID NO: 8)

D-Phe-Gln-Trp-Deg-Val-Gly-His-Leu-NH$_2$ (SEQ ID NO:9)

D-Phe-Gln-Trp-Ala-Val-Ac5c-His-Leu-NH$_2$ (SEQ ID NO: 10)

Butanoyl-D-Phe-Gln-Trp-Ala-Val-Aib-His-Leu-NH$_2$ (SEQ ID NO: 11)

Octanoyl-D-Phe-Gln-Trp-Ala-Val-Aib-His-Leu-NH$_2$ (SEQ ID NO: 12)

The present invention also envisages methods of prevention and treatment of cancer using the polypeptides of the present invention, pharmaceutical compositions comprising such polypeptides and processes for their preparation. These peptides possess antagonist properties against bombesin and bombesin-like peptides and are useful in the prevention and treatment of malignant diseases.

Suitable routes for administration of the peptides are those known in the art and include oral, rectal, transdermal, vaginal, transmucosal, or intestinal administration; parenteral delivery, including intramuscular, subcutaneous, intradedullary injections, as well as intrathecal, direct intraventricular, intravenous, intraperitoneal, intranasal, or intraocular injections.

Pharmaceutical compositions suitable for use in present invention include compositions wherein the active ingredients are contained in an effective amount to achieve its intended purpose. In addition to the active ingredients, these pharmaceutical compositions may contain suitable pharmaceutically acceptable carriers, excipients, diluents, solvents, flavorings, colorants eic. The preparations may be formulated in any form including but not limited to tablets, dragees, capsules, powders, syrups, suspensions, slurries, time released formulations, sustained release formulations, pills, granules, emulsions, patches, injections, solutions, liposomes or nanoparticles.

The exact formulation, route of administration and dosage can be chosen by the individual physician in view of the patient's condition.

The term "an effective amount" means that amount of a drug or pharmaceutical agent that will elicit the biological or medical response of a tissue, system, animal or human that is being sought. Toxicity and therapeutic efficacy of the peptides of this invention can be determined by standard pharmaceutical procedures in cell cultures or experimental animals.

The novel peptide analogs embodied in the present invention contain amino acids, namely α,α-dialkylated amino acids, which have been known to induce highly specific constraints in the peptide backbone. The α,α-dialkylated amino acids, used in the present invention are synthesized from the corresponding ketones. In a preferred embodiment of the invention, the ketones are first converted into the corresponding hydantoins which are hydrolyzed using a strong acid or base, preferably H$_2$SO$_4$, HCl, NaOH or Na$_2$CO$_3$ to yield the aforesaid amino acids. In a preferred embodiment of the present invention, 60% sulphuric acid has been employed as the hydrolyzing agent. The present invention also provides a solid phase synthesis process for the preparation of peptide analogs of the general formula (I):

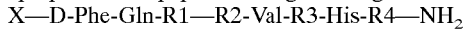

wherein X is acetyl or straight, branched, or cyclic alkanoyl group from 3–16 carbon atoms or X is deleted, R1 is Trp or D-Trp, R2 is Ala, Aib or Deg, R3 is Gly, Aib, Deg, Dpg or Ac5c, R4 is Leu or Ile which comprises sequentially loading the corresponding protected α,α-dialkylated amino acids in sequential cycles to the amino terminus of a solid phase resin, coupling the amino acids in the presence of conventional solvents and reagents to assemble a peptide-resin assembly, removing the protecting groups and cleaving the peptide from the resin to obtain a crude peptide analog.

The novel peptides in the present invention have been generated by using solid phase techniques or by a combination of solution phase procedures and solid phase techniques or by fragment condensation. These methods for the chemical synthesis of polypeptides are well known in the art (Stewart and Young, 1969, Solid Phase Peptide Synthesis, W.H. Freeman & Co.).

In a preferred embodiment of the present invention the peptides were synthesized using the Fmoc strategy, on a semi automatic peptide synthesizer (CS Bio Model 536), using optimum side chain protection. The peptides were assembled from C-terminus to N-terminus. Peptides amidated at the carboxy-terminus were synthesized using the Rink Amide resin. The loading of the first Fmoc protected amino acid was achieved via an amide bond formation with the solid support, (mediated by Diiopropylcarbodiimide (DIPCDI) and HOBt. Substitution levels for automated synthesis were preferably between 0.2 and 0.6 mmole amino acid per gram resin.

The resin employed for the synthesis of carboxy-terminal amidated peptide analogs was 4-(2',4'-Dimethoxyphenyl-Fmoc-aminomethyl)-phenoxymethyl derivatized polystyrene 1% divinylbenzene (Rink Amide) resin (100–200 mesh), procured from Calbioichem-Novabiochem Corp., La Jolla, U.S.A., (0.47 milliequivalent NH$_2$/g resin).

The N-terminal amino group was protected by 9-fluorenylmethoxy-carbonyl (Fmoc) group. Trityl (trt) or t-butyloxycarbonyl (Boc) were the preferred protecting groups for imadazole group of Histidine residue. The hydroxyl groups of Serine, Threonine and Tyrosine were preferably protected by t-butyl group (tBu) 2,2,5,7,8-pentamethyl-chroman-6-sulfonyl (Pmc) or 2,2,4,7,-pentamethyl-dihydro-benzenofuran-5 5-sulfonyl (Pbf) were the preferred protecting groups for the guandino group of Arginine. Trityl was the preferred protecting group for Asparagine and Glutamine and tertiary butyl group (tBu) was the preferred protecting group for Aspartic acid and Glutamic acid. The tryptophan residue was either left unprotected or used with Boc protection. The side chain amino group of Lysine was protected using Boc group preferably.

In a preferred embodiment of the invention, 2–8 equivalents of Fmoc protected amino acid per resin nitrogen equivalent were used. The activating reagents used for coupling amino acids to the resin, in solid phase peptide synthesis, are well known in the art. These include DCC, DIPCDI, DIEA, BOP, PyBOP, HBTU, TBTU, or HOBt. Preferably, DCC, DIPCDI/HOBt or HBTU/HOBT and DIEA were used as activating reagents in the coupling reactions.

The protected amino acids were either activated in situ or added in the form of preactivated esters known in the art such as NHS esters, Opfp esters etc. Atherton, E. et. al, 1988, J. Chem. Soc., Perkin Trans. I, 2887; Bodansky, M. in "The Peptides, Analysis, Synthesis and Biology" (E. Gross, J. Meienhofer, eds.) Vol. I, Academic Press, New York, 1979, 106.

The coupling reaction was carried out in DMF, DCM or NMP or a mixture of these solvents and was monitored by Kaiser test (Kaiser et al., Anal. Biochem., 34, 595–598 (1970)). In case of a positive Kaiser test, the appropriate amino acid was re-coupled using freshly prepared activated reagents.

After the assembly of the peptide vas completed, the amino-terminal Fmoc group was removed and then the peptide-resin was washed with methanol and dried. The peptides were then deprotected and cleaved from the resin support by treatment with trifluoroacetic acid, crystalline phenol, ethanedithiol, thioanisole and de-ionized water for 1.5 to 5 hours at room temperature. The crude peptide was obtained by precipitation with cold dry ether, filtered, dissolved, and lyophilized.

The resulting crude peptide was purified by preperative high performance liquid chromatography (HPLC) using a LICHROCART® C,8 (250. Times. 10) (reverse phase C-18 column) reverse phase column (Merck, Darmstadt, Germany) on a Preparative HPLC system (Shimadzu Corporation, Japan) using a gradient of 0.1% TFA in acetronitrile and water. The eluted fractions were reanalyzed on Analytical HPLC system (Shimadzu Corporation, Japan) using a C18 LICHROSPHERG®, WP-300 (300×4) (reverse phase C18 column) reverse-phase column. Acetronitrile was evaporated and the fractions were lyophilized to obtain the pure peptide. The identity of each peptide was confirmed by electron-splay mass spectroscopy.

Synthesis Of Peptides

A peptide of the present invention can be made by exclusively solid phase techniques, by partial solid phase/solution phase techniques and/or fragment condensation. Preferred, semi-automated, stepwise solid phase methods for synthesis of peptides of the invention are provided in the examples discussed in the subsequent section of this document.

The present invention will be further described in detail with reference to the following examples, as will be appreciated by a person skilled in the art are merely illustrative and should not be construed as limiting. Various other modifications of the invention will be possible without departing from the spirit and scope of the present invention.

EXAMPLE 1

First loading on Rink Amide Resin

A typical preparation of the Fmoc-Leu-Rink Amide Resin was carried out using 0.5 g of 4-(2',4'-Dimethoxyphenyl-Fmoc-aminomethyl)phenoxymethyl derivatized polystyrene 1% divinylbenzene (Rink Amide) resin (0.7 mM/g) (100–200 mesh), procured from Advanced Chemtech, Louisville, Ky., U.S.A., (0.7 milliequivalent $NH_2$, resin). Swelling of the resin was typically carried omit in dichloromethane measuring to volumes 10–40 ml/g resin. The resin was allowed to swell in methylene chloride (2×25 ml, for 10 min.). It was washed once in dimethylfomamide (DMF) for 1 min. All solvents in the protocol were added in 20 ml portions per cycle. The Fmoc-protecting group on the resin was removed by following steps 3–7 in the protocol. The deprotection of the Fmoc group was checked by the presence of blue beads in Kaiser test. For loading of the first amino acid on the free amino ($NH_2$) group of the resin, the first amino acid, Fmoc-Leu-OH, was weighed in three to six fold excess, along with a similar fold excess of HOBt, in the amino acid vessel of the peptide synthesizer. These were dissolved in dimethylformamide (A.C.S. grade) (J. T. Baker, Phillipsburg, N.J., U.S.A.) and activated with DIPCDI, just prior to the addition to the resin in the reaction vessel of the peptide synthesizer. HOBt was added in all coupling reactions, especially in the case of Gln and His. The coupling reaction was carried out for a period ranging from 1–3 hours. The loading of the amino acid on the resin was confirmed by the presence of colorless beads in the Kaiser Test. The loading efficiency was ascertained by the increase of weight of the resin after the addition of the amino acid.

EXAMPLE 2

Synthesis of D-Phe-Gln-Trp-Ala-Val-Aib-His-Leu-$NH_2$ (SEQ ID NO: 3)

The synthesis of SEQ ID NO: 3, amidated at the carboxyterminus, was initiated by using all of the resin loaded with Fmoc-Leu-OH as prepared in Example 1 above. This was subjected to stepwise deprotection and coupling steps as in steps 1–10 of the synthesis cycle. In each coupling reaction, a two to six fold excess of amino acid, DIPCDI and HOBt were used. Upon completion of synthesis and removal of the N-terminal Fmoc protecting group (steps 1–6 of the synthesis cycle), the peptide-resin was washed twice with methanol, dried and weighed to obtain 0.649 g. This was subjected to cleavage in a cleavage mixture consisting of trifluoroacetic acid and scavengers, ethanedithol, crystalline phenol and thioanisole and water for a period of 1.5 to 5 hours at room temperature with continuous stirring. The peptide was precipitated using cold dry ether to obtain ~330 mg of crude peptide. The crude peptide was purified on a C18 preparative reverse phase HPLC column (250×10) on a gradient system comprising acetonitrile and water in 0.1% TFA as described previously in the art. The prominent peaks were collected and lyophilized, reanalyzed on analytical HPLC and subjected to mass spectrometry.

There was a good agreement between the observed molecular weight and calculated molecular weight (Calculated Mass ~983; Observed Mass ~984.2). The pure peptide was then used for bioassays.

EXAMPLE 3

Synthesis of D-Phe-Gln-Trp-Aib-Val-Gly-His-Leu-NH₂ (SEQ ID NO:4)

The synthesis, cleavage and lyophilization steps were carried out as in the Example 2 above using the appropriate amino acids. The calculated mass was ~969 and the observed mass was 970.4.

EXAMPLE 4

Synthesis of D-Phe-Gln-D-Trp-Ala-Val-Aib-His-Leu-NH₂ (SEQ ID NO:5)

The synthesis, cleavage and lyophilization steps were carried out as in the Example 2 above using the appropriate amino acids. The calculated mass was ~983 and the observed mass was 984.30.

EXAMPLE 5

Synthesis of D-Phe-Gln-Trp-Aib-Val-Gly-His-Ile-NH₂ (SEQ ID NO:6)

The synthesis, cleavage and lyophilization steps were carried out as in the Example 2 above using the appropriate amino acids. The calculated mass was ~969 and the observed mass was 970.2.

EXAMPLE 6

Synthesis of D-Phe-Gln-Trp-Ala-Val-Aib-His-Ile-NH₂ (SEQ ID NO:7)

The synthesis, cleavage and lyophilization steps were carried out as in the Example 2 above using the appropriate amino acids. The calculated mass was ~983 and the observed mass was 984.2.

EXAMPLE 7

Synthesis of D-Phe-Gln-D-Trp-Ala-Val-Dpg-His-Leu-NH₂ (SEQ ID NO: 8)

The synthesis, cleavage and lyophilization steps were carried out as in the Example 2 above using the appropriate amino acids. The calculated mass was ~1039 and the observed mass was 1040.4.

EXAMPLE 8

Synthesis D-Phe-Gln-Trp-Deg-Val-Gly-His-Leu-NH₂ (SEQ ID NO:9)

The synthesis, cleavage and lyophilization steps were carried out as in the Example 2 above using the appropriate amino acids. The calculated mass was ~997 and the observed mass was 998.5.

EXAMPLE 9

Synthesis of D-Phe-Gln-Trp-Ala-Val-Ac5c-His-Leu-NH₂ (SEQ ID NO: 10)

The synthesis, cleavage and lyophilization steps were carried out as in the Example 2 above using the appropriate amino acids. The calculated mass was 1009 and the observed mass was 1010.4.

EXAMPLE 10

Synthesis of Butanoyl-D-Phe-Gln-Trp-Ala-Val-Aib-His-Leu-NH₂ (SEQ ID NO: 11)

The conjugation of the butanoyl group at the N-terminal position was done on solid phase. The above peptide sequence was synthesized on resin as described in Example 2. After the deprotection of D-Arg amino acid it was further coupled with butanoic acid in DMF using DIPCDI and HOBT. The cleavage and purification was further carried out following the standard protocol as described in Example 2. The final peptide was further analyzed by mass spectroscopy. The calculated mass and observed were in good agreement. (calculated mass=~1053, observed mass=1054.2).

EXAMPLE 11

Synthesis of Octanoyl-D-Phe-Gln-Trp-Ala-Val-Aib-His-Leu-NH₂ (SEQ ID NO: 12)

The conjugation of the octanoyl group at the N-terminal position after the peptide synthesized as described in Example 2 was done on solid phase using octanoic acid in DMF using DIPCDI and HOBT. The cleavage and purification was further carried out following the standard protocol as described in Example 2. The final purified peptide was further analyzed by mass spectroscopy. The calculated mass and observed were in good agreement. (calculated mass=~1109, observed mass=1110.5).

Biological Activity of Peptides

The cytotoxicity of the peptide analog was carried out by two day MTT [3-(4,5-dimethylthiazol-2-yl)-2,5-diphenyl tetrazolium bromide]assay. MTT assay is based on the principle of uptake of MTT, a tetrazolium salt, by metabolically active cells where it is metabolized by active mitochondria into a blue colored formazon product, which can be read spectrometrically (J. of Immunological Methods 65: 55–63, 1983). To prepare the MTT stock solution needed, MTT was dissolved in phosphate buffered saline with a pH of 7.4 to obtain an MTT concentration of 5 mg/ml; the resulting mixture was filtered through a 0.22 micron filter to sterilize and remove a small amount of insoluble residue. This filtered mixture was the MTT stock solution.

Briefly, for each tumor type, 10,000 cells were seeded in 96-well tissue culture plate and incubated with each peptide concentration individually in a $CO_2$ incubator for 48 hrs. The peptide analog at different concentrations was added once every 24 hrs during the incubation period. Control cultures, which were not treated with the peptide was similarly incubated. The assay was terminated by adding 100 µg (20 µl) of MTT to each well, incubating for three hours, decanting supernatant and finally adding 150 µl of dimethylsulphoxide to each well to dissolve the formazon. The plates were incubated for 15 minutes at 37° C. and read spectrophotometrically at 540 nm; and cytotoxicity percentage was calculated by following formula:

Cytotoxicity Percentage=100×[1−X/R1], where X=(absorbance of the treated sample at 540 nm-absorbance of a blank at 540 nn) and R1=(absorbance of the untreated control at 540 nm)−(absorbance of the blank at 540 nm).

Thus in each of the MTT cytotoxicity assay the percentage was calculated according to the above formula and was based on the proliferation of the untreated controls, the value of which was considered as $100\%$.

EXAMPLE 12

The biological activity of synthesized peptide SEQ ID NO:3 was tested on different human tumor cell lines such as HT-29 & PTC (colon), A549 (non small lung cell), KB (oral squamous cell), MCF7 & MDA.MB.453 (Breast), HuTu80 (duodenum), PA-1 (ovary), MOLT-4 (leukemia) and MlA-PaCa2 (Pancreas) at various molar concentrations. The percentage cytotoxicity induced by different concentrations of the peptide SEQ ID NO: 3 is summarized in the following table.

| Cell Line | Percentage cytotoxicity at different concentrations | | | | | |
|---|---|---|---|---|---|---|
| | 1 µM | 100 nM | 10 nM | 1M | 100 pM | 10 pM |
| MCF 7 | Nil | Nil | 24.35 ± 5 | 30.68 ± 6 | 38.95 ± 4.5 | 39.33 ± 2.6 |
| MIAPaCa2 | 33.3 ± 4.5 | 30.3 ± 4.2 | 33.2 ± 6.7 | 36.4 ± 0.5 | 28.2 ± 4.5 | 27.4 ± 4.5 |
| HuTu80 | 12.2 ± 4.0 | 15.5 ± 4.7 | 14.3 ± 3.5 | 13.3 ± 4.0 | 14.7 ± 4.2 | 10.3 ± 3.5 |
| KB | 32.1 ± 5.0 | 31.6 ± 6.5 | 30.9 ± 5.5 | 30.4 ± 6.5 | 26.4 ± 4.5 | 40.9 ± 5.5 |
| A549 | 30.7 ± 6.5 | 23.6 ± 4.5 | 32.2 ± 5.5 | 32.4 ± 4.5 | 25.2 ± 3.5 | 30.5 ± 3.5 |
| HT29 | 25.4 ± 5.5 | 17.8 ± 4.5 | 11.8 ± 5.0 | 20.3 ± 4.5 | 19.9 ± 5.5 | 18.7 ± 4.5 |
| PTC | 17.9 ± 2.5 | 27.7 ± 2.8 | 27.7 ± 3.6 | 23.8 ± 2.8 | 26.5 ± 3.8 | 80.0 ± 7.1 |
| MDA.MB.453 | 5.6 ± 3.5 | 11.2 ± 3.1 | Nil | 9.6 ± 1.9 | 25.5 ± 2.9 | 49.5 ± 4.2 |
| PA-1 | 31.2 ± 5.1 | 34.2 ± 5.8 | 25.4 ± 4.2 | 36.1 ± 6.1 | 40.1 ± 6.2 | 37.7 ± 3.9 |
| MOLT-4 | 9.0 ± 1.2 | 1.4 ± 1.0 | Nil | 1.0 ± 0.4 | 15.9 ± 3.0 | 49.9 ± 4.1 |

EXAMPLE: 13

The cytotoxic activity of other synthesized bombesin analogs was tested on eight human tumor cell lines namely HT-29, SW620, PTC (all colon), PA-1 (ovary), A549 (lung), HBL100(breast), MOLT-4 (leukemia) and DU145 (prostate). The tumor cells were collected at exponential growth phase and resuspended in medium ($1.5 \times 10^6$) cells/ml in RPMI 1640 containing 10% FBS). 150 µl of medium was added to the wells of a 96-well tissue culture plate (Nunc, Denmark) followed by 30 µl of cell suspension. The plate was left in incubator (37° C., 5% $CO_2$ overnight. 20 µl of the peptide ($10^{-7} \times 10^{\times 10}$M concentration) was added to marked wells of the 96-well plate. Each concentration was plated in cells served as blanks. A total volume of 200 µl was ensured in each well and plate was left in incubator (37° C., 5% $CO_2$). After 72 hours of incubation an MTT assay was performed and percentage cytotoxicity was calculated with respect to control cells. Following tables show the cytotoxicity achieved on various cell lines at different concentrations.

| S.No | Percent Cytotoxicity | | | |
|---|---|---|---|---|
| | 100 nM | 10 nM | 1 nM | 100 PM |
| PA-1 | | | | |
| SEQ ID: 4 | 2.3 ± 2.9 | 4.3 ± 0.2 | 16.2 ± 2.9 | 12.6 ± 2.9 |
| SEQ ID: 5 | 8.8 ± 1.9 | 20.9 ± 5.3 | 16.0 ± 3.9 | 25.6 ± 6.3 |
| SEQ ID: 6 | 9.2 ± 1.0 | 8.7 ± 1.9 | 7.4 ± 1.0 | 11.1 ± 2.9 |
| SEQ ID: 7 | 9.6 ± 4.1 | 22.7 ± 3.4 | 25.6 ± 2.9 | 24.5 ± 4.2 |
| SEQ ID: 8 | 10.4 ± 3.7 | 20.4 ± 3.0 | 23.8 ± 4.2 | 23.3 ± 5.5 |
| PTC | | | | |
| SEQ ID: 4 | 9.8 ± 1.7 | 2.1 ± 0.2 | 8.7 ± 1.5 | 14.9 ± 1.1 |
| SEQ ID: 5 | 20.4 ± 4.2 | 15.9 ± 2.4 | 23.0 ± 4.2 | 13.9 ± 2.2 |
| SEQ ID: 6 | 24.7 ± 5.2 | 10.4 ± 0.8 | 9.1 ± 0.7 | 10.1 ± 0.6 |
| SEQ ID: 7 | 9.3 ± 1.8 | 7.6 ± 0.7 | 12.4 ± 2.1 | 8.2 ± 0.9 |
| SEQ ID: 8 | 8.7 ± 2.1 | 5.4 ± 1.7 | 12.5 ± 1.7 | 12.3 ± 1.9 |
| DU145 | | | | |
| SEQ ID: 4 | 24.9 ± 3.2 | 23.4 ± 3.3 | 22.8 ± 4.1 | 23.2 ± 3.7 |
| SEQ ID: 5 | 32.3 ± 3.8 | 22.0 ± 3.4 | 10.6 ± 0.9 | 29.3 ± 2.9 |
| SEQ ID: 6 | 13.7 ± 0.9 | 16.6 ± | 3.9 ± 5.2 | 12.1 ± 0.8 |
| SEQ ID: 7 | NIL | NIL | ND | ND |
| SEQ ID: 8 | 19.1 ± 2.1 | 22.5 ± 2.2 | 21.4 ± 6.2 | 28.1 ± 3.5 |
| SW620 | | | | |
| SEQ ID: 4 | 34.3 ± 4.2 | 23.2 ± 2.0 | 27.8 ± 2.8 | 30.4 ± 3.2 |
| SEQ ID: 5 | 25.6 ± 4.2 | 30.1 ± 4.0 | 29.7 ± 4.2 | 38.0 ± 3.8 |
| SEQ ID: 6 | 23.5 ± 5.1 | 38.1 ± 7.3 | 33.5 ± 5.2 | 24.8 ± 4.2 |
| SEQ ID: 7 | 25.4 ± 2.9 | 20.8 ± 1.9 | 32.0 ± 5.8 | 33.6 ± 5.8 |
| SEQ ID: 8 | 29.4 ± 2.9 | 33.0 ± 3.8 | 20.6 ± 3.9 | 20.6 ± 3.9 |
| HT29 | | | | |
| SEQ ID: 4 | 38.6 ± 5.3 | 38.9 ± 7.3 | 39.6 ± 4.3 | 43.3 ± 4.4 |
| SEQ ID: 5 | 35.7 ± 2.8 | 44.4 ± 4.0 | 27.9 ± 2.9 | 42.0 ± 2.0 |
| SEQ ID: 6 | NIL | 6.8 ± 0.7 | 26.7 ± 4.2 | 16.8 ± 0.5 |
| SEQ ID: 7 | 15.5 ± 1.9 | 28.2 ± 2.8 | ND | ND |
| SEQ ID: 8 | 34.8 ± 4.2 | 18.9 ± 4.2 | 34.7 ± 3.3 | 21.4 ± 3.1 |
| MOLT4 | | | | |
| SEQ ID: 4 | 16.2 ± 0.6 | 28.7 ± 4.2 | 19.3 ± 1.8 | 28.5 ± 4.8 |
| SEQ ID: 5 | NIL | 4.3 ± 0.6 | 6.4 ± 0.2 | 8.7 ± 0.6 |
| SEQ ID: 6 | NIL | 20.4 ± 4.3 | 0.8 ± 0.1 | 11.0 ± 0.6 |
| SEQ ID: 7 | 13.1 ± 0.3 | NIL | NIL | ND |
| SEQ ID: 8 | 2.6 ± 0.1 | 12.8 ± 3.3 | 9.3 ± 0.2 | 16.6 ± 3.1 |
| HBL | | | | |
| SEQ ID: 4 | 25.0 ± 3.1 | 33.2 ± 5.2 | 30.6 ± 4.2 | 33.0 ± 3.6 |
| SEQ ID: 5 | 19.4 ± 4.5 | 16.7 ± 3.6 | 31.6 ± 5.3 | 19.3 ± 2.7 |
| SEQ ID: 6 | 17.0 ± 0.5 | 6.0 ± 0.4 | 1.2 ± 0.3 | NIL |
| SEQ ID: 7 | 16.1 ± 3.9 | 7.0 ± 0.7 | 12.0 ± 0.7 | 4.0 ± 0.6 |
| SEQ ID: 8 | 11.9 ± 2.1 | 14.4 ± 2.1 | 12.2 ± 1.9 | 12.1 ± 1.9 |
| A549 | | | | |
| SEQ ID: 4 | 20.0 ± 2.2 | 20.6 ± 1.9 | 22.7 ± 2.9 | 20.7 ± 4.2 |
| SEQ ID: 5 | 30.3 ± 4.3 | 22.2 ± 3.1 | 20.2 ± 4.2 | 25.2 ± 5.6 |

-continued

| | Percent Cytotoxicity | | | |
|---|---|---|---|---|
| S.No | 100 nM | 10 nM | 1 nM | 100 PM |
| SEQ ID: 6 | 1.9 ± 0.6 | 3.2 ± 0.1 | 13.0 ± 0.8 | 12.4 ± 0.7 |
| SEQ ID: 7 | 6.7 ± 2.0 | 17.9 ± 0.9 | ND | ND |
| SEQ ID: 8 | 21.7 ± 3.3 | 20.7 ± 2.2 | 19.7 ± 3.1 | 17.0 ± 2.7 |

EXAMPLE 14

The cytotoxic effect of peptide sequences SEQ ID NO: 9, SEQ ID NO: 10, SEQ ID NO: 11 and SEQ ID NO: 12, were studied by MTT assay which is based on the principle of uptake of MTT[3-[4,5-dimethylthiazol-2-yl]-2,5-diphenyl tetrazolium bromide], a tetrazolium salt by the metabolically active cells where it is metabolized by active mitochondria into a blue colored formazan product which can be read spectrophotometrically. Tumor cells KB (oral squamous). HuTu80 (Stomach), PTC and SW620 (colon), U87MG (Glioblastoma), HBL 100. (Breast), HeP2 (laryngeal) and L132 (Lung) were incubated with the peptide analogs for 48 hours at 37° C. in a 96-well culture plate, followed by the addition of 100 μl MTT and further incubation of 1 hour. The formazon crystals formed inside the cells were dissolved with a detergent comprising 10% Sodium dodecyl sulfate and 0.01 N HCl and optical density read on a multiscan ELISA reader. The optical density was directly proportional to the number of proliferating and metabolically active cells. Percent cytotoxicity of peptide analogs is shown in the following Table.

| Cell | Percentage cytotoxicity at different concentrations | | | | | |
|---|---|---|---|---|---|---|
| | 1 μM | 100 nM | 10 nM | 1 nM | 100 pM | 10 pM |
| | SEQ ID: 9 | | | | | |
| KB | 10.4 ± 1.6 | 20.8 ± 1.7 | 23.0 ± 2.1 | 32.6 ± 3.7 | 26.9 ± 2.9 | 20.6 ± 4.1 |
| HuTu80 | 14.2 ± 0.6 | 13.5 ± 2.1 | 23.5 ± 2.9 | 28.0 ± 1.8 | 23.8 ± 2.8 | 19.5 ± 0.4 |
| PTC | 10.3 ± 0.9 | 19.5 ± 4.1 | 26.8 ± 3.8 | 25.6 ± 5.1 | 24.5 ± 3.9 | 22.4 ± 2.2 |
| U87MG | 10.0 ± 0.0 | 21.4 ± 0.1 | 20.0 ± 0.0 | 21.8 ± 0.1 | 11.9 ± 4.1 | 0.0 ± 0.0 |
| SW620 | 21.6 ± 2.1 | 25.8 ± 2.8 | 33.2 ± 2.9 | 30.8 ± 0.6 | 28.9 ± 0.2 | 15.1 ± 0.3 |
| HBL100 | 17.2 ± 0.4 | 22.4 ± 1.7 | 28.1 ± 0.6 | 34.1 ± 1.8 | 28.6 ± 2.2 | 17.2 ± 0.1 |
| HeP2 | 21.6 ± 1.8 | 17.8 ± 0.3 | 28.5 ± 3.1 | 21.3 ± 2.2 | 14.6 ± 0.6 | 0.0 ± 0.0 |
| L132 | 18.3 ± 2.9 | 25.9 ± 2.6 | 27.2 ± 3.1 | 30.5 ± 4.1 | 22.4 ± 0.8 | 0.0 ± 0.0 |
| | SEQ ID: 10 | | | | | |
| KB | 16.5 ± 0.2 | 22.0 ± 1.1 | 27.3 ± 2.7 | 31.1 ± 4.1 | 25.0 ± 6.3 | 19.2 ± 2.9 |
| HuTu80 | 17.2 ± 1.1 | 21.0 ± 2.0 | 20.6 ± 1.7 | 23.3 ± 2.8 | 22.9 ± 0.2 | 13.5 ± 0.8 |
| PTC | 28.4 ± 3.6 | 29.3 ± 3.2 | 32.5 ± 5.1 | 29.4 ± 2.9 | 21.6 ± 3.1 | 22.2 ± 4.9 |
| U87MG | 10.0 ± 0.0 | 15.0 ± 0.5 | 20.0 ± 0.0 | 25.6 ± 2.1 | 16.5 ± 0.5 | 11.6 ± 1.7 |
| SW620 | 22.2 ± 2.1 | 19.4 ± 1.8 | 25.5 ± 2.8 | 22.4 ± 1.7 | 20.9 ± 0.6 | 16.7 ± 0.2 |
| HBL100 | 18.5 ± 1.7 | 21.2 ± 1.7 | 32.9 ± 0.7 | 23.3 ± 1.6 | 16.6 ± 0.1 | 21.1 ± 0.7 |
| HeP2 | 19.9 ± 1.5 | 26.3 ± 1.7 | 27.5 ± 2.8 | 27.2 ± 2.6 | 19.1 ± 0.6 | 1.7 ± 0.1 |
| L132 | 22.4 ± 1.8 | 27.8 ± 2.1 | 27.5 ± 2.8 | 29.5 ± 2.8 | 29.4 ± 1.9 | 1.9 ± 0.2 |
| | SEQ ID: 11 | | | | | |
| KB | 24.2 ± 1.2 | 31.9 ± 2.1 | 31.9 ± 3.1 | 33.1 ± 2.1 | 26.7 ± 5.1 | 21.6 ± 3.7 |
| HuTu80 | 14.2 ± 0.1 | 20.0 ± 3.1 | 27.3 ± 2.7 | 30.5 ± 4.1 | 22.6 ± 3.9 | 17.6 ± 1.6 |
| PTC | 18.6 ± 1.5 | 25.8 ± 2.5 | 25.7 ± 4.1 | 28.5 ± 2.8 | 28.3 ± 0.8 | 19.7 ± 0.6 |
| U87MG | 1.0 ± 0.1 | 15.5 ± 0.6 | 20.0 ± 0.0 | 24.2 ± 1.7 | 26.5 ± 2.6 | 21.9 ± 2.1 |
| SW620 | 23.7 ± 1.4 | 21.0 ± 1.5 | 31.5 ± 2.6 | 35.1 ± 2.2 | 25.9 ± 3.8 | 20.4 ± 0.3 |
| HBL100 | 24.5 ± 0.8 | 22.7 ± 0.5 | 29.9 ± 0.3 | 24.3 ± 1.6 | 15.4 ± 4.1 | 18.2 ± 1.1 |
| HeP2 | 21.9 ± 2.1 | 23.9 ± 1.1 | 34.6 ± 2.2 | 37.1 ± 3.3 | 20.1 ± 0.0 | 15.1 ± 0.3 |
| L132 | 1.4 ± 1.1 | 20.4 ± 1.5 | 30.4 ± 0.4 | 29.4 ± 0.4 | 18.3 ± 0.9 | 0.5 ± 0.0 |
| | SEQ ID: 12 | | | | | |
| KB | 12.4 ± 1.2 | 11.1 ± 3.1 | 18.6 ± 2.1 | 26.6 ± 4.9 | 19.4 ± 2.9 | 19.3 ± 2.9 |
| HuTu80 | 20.0 ± 3.9 | 21.8 ± 2.1 | 23.4 ± 0.5 | 33.1 ± 4.8 | 13.0 ± 0.7 | 8.3 ± 1.1 |
| PTC | 14.4 ± 2.7 | 16.1 ± 2.5 | 20.7 ± 3.8 | 30.1 ± 4.1 | 18.6 ± 2.4 | 19.5 ± 0.8 |
| U87MG | 15.4 ± 3.1 | 13.1 ± 2.3 | 27.5 ± 2.9 | 28.3 ± 1.9 | 22.1 ± 3.8 | 13.1 ± 2.2 |
| SW620 | 22.6 ± 1.1 | 25.3 ± 0.6 | 36.1 ± 1.9 | 32.2 ± 2.6 | 38.4 ± 2.8 | 34.8 ± 0.4 |
| HBL100 | 11.8 ± 1.1 | 23.6 ± 2.7 | 27.7 ± 1.5 | 29.6 ± 0.4 | 34.7 ± 2.8 | 29.0 ± 3.8 |
| HeP2 | 28.7 ± 0.8 | 25.6 ± 0.4 | 29.2 ± 1.1 | 28.9 ± 0.5 | 24.4 ± 0.1 | 10.0 ± 0.0 |
| L132 | 22.2 ± 0.2 | 22.0 ± 0.1 | 26.4 ± 0.3 | 26.7 ± 0.4 | 23.1 ± 0.7 | 0.0 ± 0.0 |

All publications referenced are incorporated by reference herein, including the nucleic acid sequences acid sequences and amino acid sequences listed in each publication. All the compounds and methods disclosed and referred to in the publications mentioned above are incorporated by reference herein, including those compounds disclosed and referred to in articles cited by the publications mentioned above.

What is claimed is:

1. A peptide of the formula

X-D-Phe-Gln-R1-R2-Val-R3-His-R-4-NH$_2$ wherein X is acetyl or straight, branched or cyclic alkanoyl group from 3–16 carbon atoms, or X is deleted R1 is Trp or D-Trp, R2 is Ala, Aib or Deg, R3 is Gly, Aib, Deg, Dpg or Ac5c, R4 is Leu or Ile wherein at least one of R2 or R3 is an α,α-dialkylated amino acid; or a pharmaceutically acceptable salt of the peptide wherein Aib is α-aminoisobutyric acid, Deg is α,α-diethyl glycine, Dpg is α,α-di-n-propyl glycine and Ac5c is 1-amino-cyclo pentane carboxylic acid.

2. The peptide of claim 1, wherein X is deleted, R1 is Trp, R2 is Ala, R3 is Aib and R4 is Leu, and said peptide has the formula:

D-Phe-Gln-Trp-Ala-Val-Aib-His-Leu-NH$_2$ (SEQ ID NO: 3)

or a pharmaceutically acceptable salt thereof.

3. A composition comprising a peptide according to claim 2, and a pharmaceutically acceptable carrier.

4. The peptide of claim 1, wherein X is deleted, R1 is Trp, R2 is Aib, R3 is Gly and R4 is Leu, and said peptide has the formula:

D-Phe-Gln-Trp-Aib-Val-Gly-His-Leu-NH$_2$ (SEQ ID NO: 4)

or a pharmaceutically acceptable salt thereof.

5. A composition comprising a peptide according to claim 4, and a pharmaceutically acceptable carrier.

6. The peptide of claim 1, wherein X is deleted, R1 is D-Trp, R2 is Ala, R3 is Aib and R4 is Leu, and said peptide has the formula:

D-Phe-Gln-D-Trp-Ala-Val-Aib-His-Leu-NH$_2$ (SEQ ID NO:5)

or a pharmaceutically acceptable salt thereof.

7. A composition comprising a peptide according to claim 6, and a pharmaceutically acceptable carrier.

8. The peptide of claim 1, wherein X is deleted, R1 is Trp, R2 is Aib, R3 is Gly and R4 is Ile, and said peptide has the formula:

D-Phe-Gln-Trp-Aib-Val-Gly-His-Ile-NH$_2$ (SEQ ID NO: 6)

or a pharmaceutically acceptable salt thereof.

9. A composition comprising a peptide according to claim 8, and a pharmaceutically acceptable carrier.

10. The peptide of claim 1, wherein X is deleted, R1 is Trp, R2 is Ala, R3 is Aib and R4 is Ile, and said peptide has the formula:

D-Phe-Gln-Trp-Ala-Val-Aib-His-Ile-NH$_2$ (SEQ ID NO:7)

or a pharmaceutically acceptable salt thereof.

11. A composition comprising a peptide according to claim 10, and a pharmaceutically acceptable carrier.

12. The peptide of claim 1, wherein X is deleted, R1 is D-Trp, R2 is Ala, R3 is Dpg and R4 is Leu, and said peptide has the formula:

D-Phe-Gln-D-Trp-Ala-Val-Dpg-His-Leu-NH$_2$ (SEQ ID NO:8)

or a pharmaceutically acceptable salt thereof.

13. A composition comprising a peptide according to claim 12, and a pharmaceutically acceptable carrier.

14. The peptide of claim 1, wherein X is deleted, R1 is Trp, R2 is Deg, R3 is Gly and R4 is Leu, and said peptide has the formula:

D-Phe-Gln-Trp-Deg-Val-Gly-His-Leu-NH$_2$ (SEQ ID NO:9)

or a pharmaceutically acceptable salt thereof.

15. A composition comprising a peptide according to claim 14, and a pharmaceutically acceptable carrier.

16. The peptide of claim 1, wherein X deleted, R1 is Trp, R2 is Ala, R3 is Ac5c and R4 is Leu, and said peptide has the formula:

D-Phe-Gln-Trp-Ala-Val-Ac5c-His-Leu-NH$_2$ (SEQ ID NO: 10)

or a pharmaceutically acceptable salt thereof.

17. A composition comprising a peptide according to claim 16, and a pharmaceutically acceptable carrier.

18. The peptide of claim 1, wherein X is butanoyl, R1 is Trp, R2 is Ala, R3 is Aib and R4 is Leu, and said peptide has the formula:

Butanoyl-D-Phe-Gln-Trp-Ala-Val-Aib-His-Leu-NH$_2$ (SEQ ID NO: 12) or a pharmaceutically acceptable salt thereof.

19. A composition comprising a peptide according to claim 18, and a pharmaceutically acceptable carrier.

20. The peptide of claim 1, wherein X is octanoyl, R1 is Trp, R2 is Ala, R3 is Aib and R4 is Leu and said peptide has the formula:

Octanoyl-D-Phe-Gln-Trp-Ala-Val-Aib-His-Leu-NH$_2$ (SEQ ID NO: 12) or a pharmaceutically acceptable salt thereof.

21. A composition comprising a peptide according to claim 20, and a pharmaceutically acceptable carrier.

22. A composition comprising a peptide according to claim 1, and a pharmaceutically acceptable carrier.

* * * * *